United States Patent [19]

Cohen et al.

[11] Patent Number: 4,817,627

[45] Date of Patent: Apr. 4, 1989

[54] ELECTROENCEPHALOGRAPHIC MONITORING

[75] Inventors: Daniel E. Cohen, Eden Prairie; Frederick T. Strobl, Wayzata, both of Minn.

[73] Assignee: CNS, Inc., Eden Prairie, Minn.

[21] Appl. No.: 93,577

[22] Filed: Sep. 4, 1987

Related U.S. Application Data

[63] Continuation-in-part of Ser. No. 83,666, Aug. 7, 1987, abandoned.

[51] Int. Cl.⁴ .............................................. A61B 5/04
[52] U.S. Cl. .................................................... 128/731
[58] Field of Search .................. 128/731, 732, 733

[56] References Cited

U.S. PATENT DOCUMENTS

| | | |
|---|---|---|
| 3,760,796 | 9/1973 | Baessler et al. ............... 128/2.1 |
| 4,214,591 | 7/1980 | Sato et al. ..................... 128/731 |
| 4,254,779 | 3/1981 | Miyata et al. ................. 128/731 |
| 4,279,258 | 7/1981 | John ............................. 128/731 |
| 4,412,547 | 11/1983 | Callahan et al. ............. 128/731 |
| 4,417,592 | 11/1983 | John ............................. 128/731 |
| 4,557,270 | 12/1985 | John ............................. 128/731 |
| 4,579,125 | 4/1986 | Strobl et al. ................. 128/731 |
| 4,610,259 | 9/1986 | Cohen et al. ................ 128/731 |

Primary Examiner—Francis Jaworski
Assistant Examiner—George Manuel
Attorney, Agent, or Firm—Kinney & Lange

[57] ABSTRACT

A method and apparatus for obtaining an indication of the extent and duration of reduced power in electroencephalographic signals as a basis for determining whether blood flow to the human brain providing such signals needs to be increased.

43 Claims, 4 Drawing Sheets

ELECTROENCEPHALOGRAPHIC MONITORING

This is a continuation-in-part of application Ser. No. 07/083,666, filed Aug. 7, 1987.

BACKGROUND OF THE INVENTION

1. Field of the Invention

The present invention relates to electroencephalographic signal monitoring and, more particularly, to the monitoring of conditions reflected in electroencephalographic signals through an indicator based on such signals.

Situations occur in which the cerebral perfusion pressure can be insufficient to the point where parts of the human brain have a supply of blood so insufficient as to put a patient at risk of neurologic damage. Such situations can arise, for instance, in surgeries utilizing cardiopulmonary bypass machines, i.e. a heart-lung machine. Such a machine serves as a pump and oxygenator to supply oxygenated blood in place of the heart and lungs during such surgery, for instance, open-heart surgery. Other surgery situations which could interfere with brain blood flow are carotid endarterectomies and cerebral aneurysm repairs.

The sufficiency of the cerebral perfusion pressure is reflected to a considerable extent in the electroencephalographic signals obtained from such a subject or patient. Electroencephalographic signals are minute electrical signals produced in the brain. An electroencephalograph measures the electrical potential at the surface of the scalp of the patient's head by the use of electrodes pasted to the surface of the scalp typically at one or more of the standard positions adopted by the International Federation of Electroencephalography in what is called the 10/20 system.

There can be as many as 20 electrodes provided in this manner which are connected to electroencephalographic equipment to provide indications of the potentials measured. These potentials are typically in the range of 1 to 200 $\mu V$.

The electrical potentials measured and represented as electroencephalographic signals have been found to provide a relatively sensitive indication of whether adequate blood flow is being maintained in the brain. Cerebral perfusion pressure must not drop too far for too long a period of time, or a cerebral disorder may result because of the lack of oxygen to the brain or because of disturbances in the brain's cellular metabolism. The necessary blood flow in the brain, however, varies from individual to individual, depending on the characteristics of the patient including age, metabolism and the like. Thus, a convenient indicator from a set of electroencephalographic signals being monitored would be desirable even though there are no absolute criteria.

SUMMARY OF THE INVENTION

The present invention provides a method for obtaining an indicator of the extent and duration of reduced power in the electroencephalographic signals based on a succession of total powers found for a corresponding succession of time segments in such a signal. These signals can be sampled to provide a sequence of samples one for each subsequence for each time segment, which sequences can each also be viewed as sequences of these subsequences. These subsequences have frequency domain power spectra found therefor, some of which can be averaged together to form a succession of average frequency domain power spectra for which a succession of corresponding total powers is found. Alternatively, a total spectral power for each such frequency domain power spectrum for a subsequence can be determined, and some of these can be averaged together to form such a succession of total powers. A parameter index based on these total powers, which is monotonic, provides an indication of the extent and duration of significant reductions in such a succession of total powers. The index is the basis for determining whether blood flow to the brain is to be changed. The apparatus for acquiring such electroencephalographic signals and providing such succession of total powers and index also provides a display thereof.

DETAILED DESCRIPTION OF THE PREFERRED EMBODIMENTS

Electroencephalographic signals are analog signals which must be sampled in amplitude over a selected interval of time with each such sample converted to its digital equivalent value if such signals are to be treated by a digital computer. Although treating these signals somewhat further, or completely, by analog signal processing means is possible, such methods are not nearly as convenient as digital methods, nor as accurate. These consecutive digitized samples, consecutive in the time order in which they are obtained from the sampled signal, can have the power thereof assessed most conveniently if they are transformed from the time domain to the frequency domain by some fast Fourier transform (FFT) algorithm. The results of the transformation represent a frequency spectrum from which the power spectrum can be obtained in a well known manner.

Figure 1:
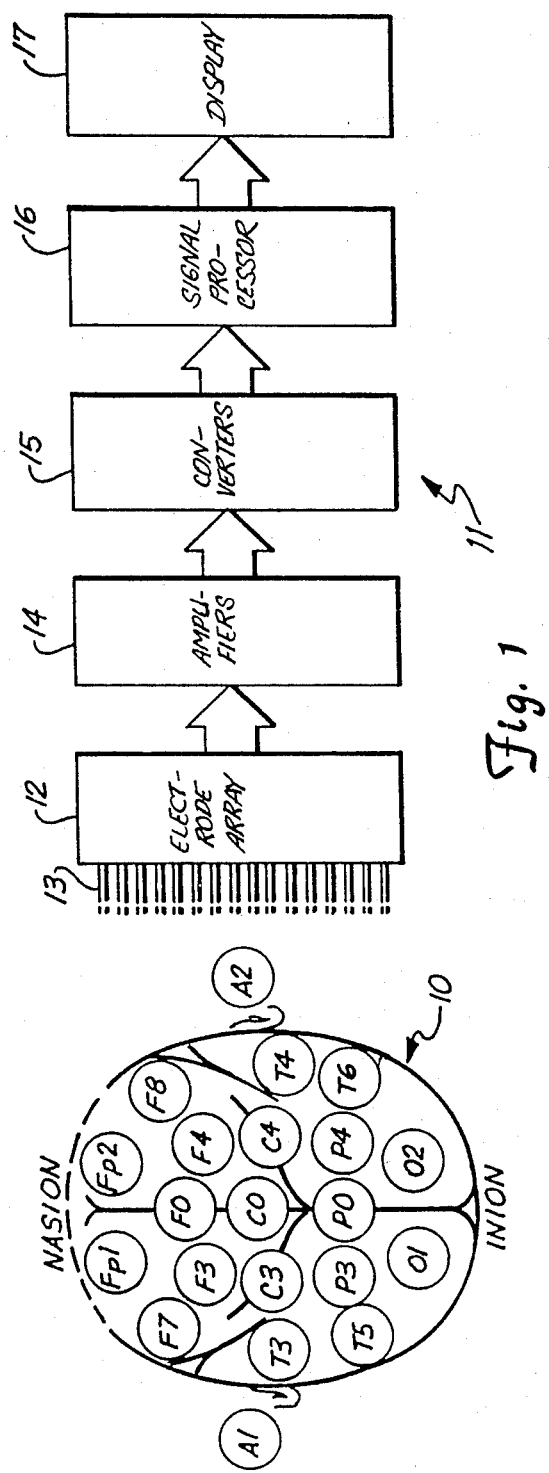
FIG. 1 shows a block diagram of the present invention.

FIG. 1 shows the top of a subject's or patient's head, 10, and the standard positions on the scalp thereof for locating electrodes for electroencephalographic monitoring. The locations for the electrodes are identified by the commonly used designations Fp1, Fp2, F0, F3, F4, F7, F8, T3, T4, T5, T6, C0, C3, C4, P0, P3, P4, O1 and O2. There are also shown reference electrode locations A1 and A2 for the attachment of reference electrodes, these being commonly attached to one or both of the patient's ears. These standard positions can be, but need not be, used for present purposes.

To the right of head 10 in FIG. 1 is an electroencephalographic signal analyzing system, 11. Analyzer system 11 has an electroencephalographic electrode array module, 12, which has extending therefrom, though arbitrarily shortened in FIG. 1 to avoid obscurance, coupling cables, 13. Typically, there are 16 electrodes for acquiring signals with one each provided on the distal end of each of coupling cables 13. A further electrode is on one of cables 13 for attachment as a reference, typically to an ear but other connection possibilities exist and are frequently used. Electrodes need not be shown in FIG. 1 because they are well known pieces of standard equipment available for use with electroencephalographic testing. The electrodes not shown are intended to be placed at one of the designated locations shown on head 10. Depending on the nature of the monitoring, there may be fewer than 16 electrodes used in gathering data in any one monitoring arrangement, but there may also be more.

The signals obtained by electrode array module 12 are transmitted to an amplifying system, 14, which contains one amplifier for each of cables 13. Typically, each of these amplifiers is a differential amplifier and measures the signal transmitted by its corresponding coupling cable 13 connected to electrodes at adjacent positions on the subject's or patient's head 10. A typical alternative would be to connect the corresponding cable 13 to measure the signals at a position on head 10 with respect to one or both locations A1 and A2 on head 10. These amplifiers provide a gain on the order of 70,000 and can amplify signals containing frequencies up to several tens of hertz without degredation because of any frequency response limits of the amplifier. Such amplifiers need not be further described as they are well known for use in electroencephalographic monitoring.

The amplified electroencephalographic analog signals are provided from amplification module 14 to an analog multiplexer and then to an analog-to-digital converter containing a conversion module, 15. Consecutive samples, taken over a selected time interval, of the amplitude of each electrode acquired analog signal have digital values provided therefor in conversion module 15 in a well known manner. Conversion module 15 has been found to provide adequate resolution for the present state of the art if an analog sample is converted into a digital representation as a binary number of 12 magnitude bits and a sign bit.

As is well known, the taking of samples is repeated at fixed intervals at a rate or frequency which must exceed twice the highest frequency in the electroencephalographic signal which is to be represented by the samples if that signal is to be fully represented. Thus, if the upper frequency content of a signal is uncertain, sampling rates should be increased accordingly to the point where there is no longer any concern about having exceeded twice the highest rate signal. A way of assuring that the upper frequency is known for sapling purposes is to pass that signal through a filter. A typical sampling rate for module 15 in these circumstances would be 256 hz, a rate adequate for the present state of the art if the electroencephalographic signal has passed through a low pass filter with a cutoff frequency set at 35 hz with an 18 db per octave rolloff. Converters capable of the performance described in this paragraph are well known and readily available, and so require no further description here.

Digitized samples provided in conversion module 15 are provided to a signal processing means, 16. Digitized samples from each of the signals obtained from a scalp location on head 10 are analyzed there to determine the changes in spectral power occurring therein (as an indicator of cerebral perfusion) because of other situations occurring in the patient's or subject's body affecting head 10. The results obtained in signal processing means 16 are transmitted to a display module, 17, where they can be presented to an operator. Such a display module may be a video terminal, printer, or other convenient means.

Figure 2:
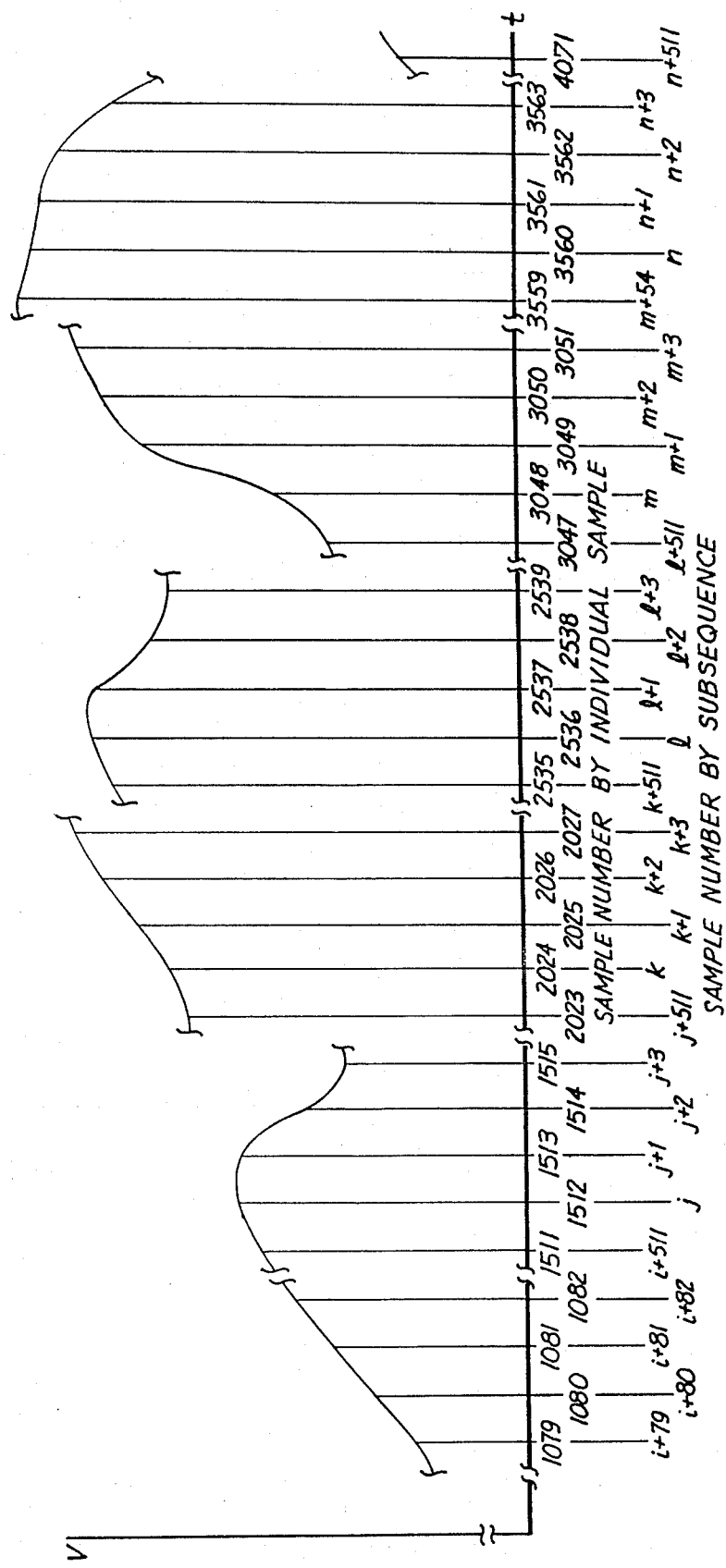
FIG. 2 shows a signal obtained in the system of FIG. 1.

A portion of a typical electroencephalographic analog, voltage signal waveform transmitted by one of the coupling, or data gathering, cables 13 is shown in FIG. 2 where the origin along the time axis has been set to zero at an arbitrary point. The measured electrical potential appearing in the signal is plotted on the vertical axis as a voltage, v. Thin vertical lines intersecting the waveform are drawn from the waveform across the time axis down to a number which represents the number of the sample taken for that point of the waveform portion shown.

Note that breaks in both the time axis and the voltage axis are indicated near the origin so that this graphic represents just a particular portion of the signal waveform example chosen for illustration. That is, there is no significance in having chosen samples beginning with 1079 other than illustrating an arbitrary portion of a typical waveform. The entire waveform for each of cables 13 would be acquired over an interval of time typically measured, for example, in hours for a major surgical procedure such as open-heart surgery accompanied by the use of a heart-lung machine. The actual digitized voltage values for the samples shown in FIG. 2 are not given as these are unnecessary for purposes of explanation.

The consecutive samples ordered by time are numbered consecutively by the first numbering sequence in FIG. 2, this numbering of the samples from this signal being designated as SAMPLE NUMBER BY INDIVIDUAL SAMPLE. The portion of the waveform shown begins with sample number 1079, goes to sample number 1082, where a break is shown along the time axis and in the waveform such that the next sample shown is sample number 1511. This pattern of breaks in the time axis, and correspondingly in the waveform, is continued along the time axis so that only portions of the waveform are shown while large portions of the waveform between samples 1079 and 4071 are omitted.

This breaking into portions of the waveform, and of corresponding portions of the time axis, was done to permit showing a renumbering of the samples on the basis of dividing them up into subsequences corresponding to segments of the waveform. That is, the sequence of individual samples is considered from the viewpoint of being a consecutive sequence of such subsequences which together provide the same sequence of samples as the original sequence of samples taken of the example waveform. This second numbering of those same samples covered by the first numbering is designated in FIG. 2 as SAMPLE NUMBER BY SUBSEQUENCE.

This numbering by subsequence is shown with the $i^{th}$ subsequence arbitrarily beginning with that sample numbered 1000 from the first numbering which then serves as the zeroth sample in this $i^{th}$ subsequence. This $i^{th}$ subsequence continues through sample 1511 in the first numbering method which serves as the last sample in the $i^{th}$ subsequence, or sample number $i+511$ in the second numbering method. Immediately thereafter begins the $j^{th}$ subsequence with the zeroth sample in that subsequence designated j in the second numbering method and continuing through $j+511$. These second numbering method numbers in the $j^{th}$ subsequence correspond to samples numbered 1512 through 2023 in the first numbering method. This sort of relationship between the first and second numbering methods continues in the other portions of the example waveform shown in FIG. 2, continuing through the $k^{th}$, $l^{th}$, $m^{th}$ and $n^{th}$ subsequences.

Thus, the sequence of samples of the example waveform portion shown in FIG. 2 can be considered as either a set of consecutive individual samples ordered in time, or a set of consecutive subsequences ordered in time with the consecutive samples in each subsequence also ordered in time. In effect, each subsequence covers a selected duration of time along the time axis in FIG. 2, the durations shown in this example, each containing 512 individual samples of a waveform segment. The sequence of subsequences of samples of the example electroencephalographic voltage signal shown can be represented as a $v_j(t_i)$, where j is an integer representing the number of a subsequence (any of the letters in the subsequence numbering of FIG. 2) and i is an integer representing the number of a time sample point within a subsequence (number after a letter in the subsequence numbering of FIG. 2) and which can range from 0 to 511. Thus, a subsequence lasts 2 seconds at the chosen sampling rate of 256 samples per second. There need be no particular limit over which j can range. Hence, conversion module 15 presents each $v_j(t_i)$ as a subsequence of samples for one electroencephalographic signal to signal processing module 16.

Signal processing module 16 receives consecutive $v_j(t_i)$ for each electroencephalographic signal and provides an estimate of the power spectrum for that set of samples contained in each subsequence for each signal. Thus, there is a succession of power spectra formed for each signal, one spectrum formed for each consecutive subsequence of samples provided for that signal, leading to a plurality of power spectra successions considering all of the signals. (Some subsequences may not have spectra formed therefor or, if formed, not further used in the system if they are found too badly contaminated with electroencephalographic artifacts or noise.)

Such power spectra are established, as indicated, by use of transform techniques selected from many well known techniques to transform the signals from the time domain to the frequency domain such as the fast Fourier transform technique. Power spectra of such transformed signals are then estimated by a selected one of well known techniques and can be represented as $V^2(f_k)$ where k is an integer which is the number of a frequency point for which a value is presented in a spectrum (not the subsequence numbering k in FIG. 2). One representation that has been found sufficient is provided by having a frequency component at every half hertz through 30 hertz so that k ranges from 1 through 60.

Such power spectra, properly presented for consideration by a trained observer for each electroencephalographic signal, can provide telling indicators as to whether or not sufficient cerebral perfusion is being maintained in the human brain. A first decision for the presentation of this data is the length of those periods over which data is to be accumulated as a basis for providing statistical parameters useful in gauging such perfusion. Such a period of time should be long enough to avoid an unnecessary multiplicity of findings of such statistical parameters, but short enough to be sensitive to the fastest significant changes likely to occur in the blood flow system. A period of time of one minute to update statistical parameters based on the gathering of additional data from the electroencephalographic signals has been found satisfactory.

With this choice for an update, and because each subsequence covers approximately two seconds in this example as indicated above, there will be about 30 subsequences of samples for each signal formed in each update period to provide the basis for presentations of indicators of cerebral perfusion, and for providing the underlying statistical parameters. However, in practice, some of the subsequences may not be selected for use in forming statistics, again because of unusual value patterns therein indicating that some signal disturbance occurred leading to data being provided which should not be used. Thus, the updating period could be made variable in time to a sufficient extent so as to provide thirty usable subsequences of data in each, or could be a constant duration update period which could contain less than thirty subsequences of useful data. To avoid unnecessarily complicating the situation, the power spectra in this example will be presented as though they are provided in one to one correspondence with the subsequences and so will be represented as $V_j^2(f_k)$.

The total power in an electroencephalographic signal during an update period can be found based on first providing an average power spectrum for that update period, thereby leading to a succession of average power spectra with there being one for each update period. This average is found by averaging each frequency component in each of the n power spectra provided in an update period, or for the $m^{th}$ (not the m of FIG. 2) update period (each having a duration of u)

$$V_m^2(f_k)_{avg} = \sum_{j=1}^{n} \frac{V_j^2(f_k)}{n}.$$

Then the total power for the $m^{th}$ update period can be found by summing the average power occurring at each frequency component point in the average spectrum as follows:

$$P_m = \sum_{k=1}^{60} V_m^2(f_k)_{avg}.$$

Thus, there will be a succession of total powers, $P_m$, one for each update period m. Each of the other electroencephalographic signals will also have a succession of average powers formed therefor in successive update periods, and a succession of total powers found therefor in this same sequence of update peiods.

Alternatively, the total power in the electroencephalographic signal in an update period can be found by finding the total power in each of the n power spectra provided in an update period, the total power for the $j^{th}$ subsequence being:

$$P_j = \sum_{k=1}^{60} V_j^2(f_k)$$

The total power for the $m^{th}$ update period is then the average of these subsequence total powers or:

$$P_m = \sum_{j=1}^{n} \frac{P_j}{n}$$

Because of the varying characteristics from patient to patient, a succession of total powers in a sequence of update periods during the time of an operation provides a better indication to an observer if this succession of total powers is related to those electroencephalographic powers which occur in the patient's brain in more ordinary circumstamnces. These are the circumstances existing just prior to a critical step in the procedure after anesthesia such as the step of converting to reliance on external means to maintain the patient's perfusion. If such data concerning electroencephalographic signal power levels occurring in a brain prior to such a critical step during surgery is to be available during that step of the surgery, a reference set of electroencephalographic signal measurements must be made in anticipation of the critical step but prior thereto. The time of taking of such reference data could be immediately before the start of the critical step, though usually after anesthesia, or at some earlier time depending on the judgment of the operator as to the time to obtain the best data.

In the obtaining of such reference data, exactly the same arrangement is used to obtain the data as has been described above for use during critical steps of the surgery—the procedure is merely done in an earlier time period. This reference data should be obtained for a time of at least a few update periods. Perhaps a minimum would be three minutes total of data which is free of unusual disturbances in any of the electroencephalographic signals during such time. During such a time, a sequence of samples for each electroencephalographic signal to be monitored during the later surgery would be obtained and subsequences thereof, found in the manner above, would have corresponding successions of power spectra found therefor. Corresponding successions of average power spectra would then be found, one for each update period. The corresponding total powers in each of those update periods would then be found to thereby form successions of total powers.

A useful reference power measure is then obtained through averaging this succession of reference update period total powers $P_{m:base}$ for each electroencephalographic signal. If s update periods are included, the total power to be used as the reference or base power against which to relate the successions of total powers found during the subsequent surgery would be obtained from the following:

$$P_{base} = \sum_{m=1}^{s} \frac{P_{m:base}}{s}$$

Such a reference or base power is obtained in this manner for each electroencephalographic signal obtained during the base line or reference data gathering period.

From the foregoing statistics, two parameters can be provided as indicators of whether sufficient cerebral perfusion is being maintained in the brain of a patient from which such electroencephalographic signals are obtained. The first of these parameters is the trend of time of the ratio of the total power in each delectroencephalographic signal to the reference power $P_{base}$ found for that signal in the base line or reference data gathering process. This parameter is most easily presented to the operator in the form of a graph of the ratio expressed as a percentage versus time over a sufficient amount of time to cover critical portions of any surgery or other procedure the patient is undergoing.

The graphs of this parameter resulting for each of the acquired electroencephalographic signals, and the graphs of the second parameter described below, are shown in three instances in FIGS. 3A, 3B and 3C as they would be presented on a display screen of a video terminal. Sixteen electroencephalographic signals have been acquired to provide the data resulting in sixteen separate, corresponding graphs each enclosed in the display in a separate rectangular outline or "box". Each of these figures shows the results obtained for a different patient who has undergone open-heart surgery. The separate electroencephalographic signal data representation in each of the boxes has the ratio percentage plotted along the vertical scale with a 0% value occurring at the bottom horizontal line of the box and 100% at the top horizontal line of the box. Two horizontal dashed lines extending from the left side of each box to the right side are provided at the 10% ratio and at the 40% ratio level, the latter also being, in this example, the threshold level for the power drop index or PDI as the second parameter which will be described below.

The horizontal bottom line of each of the signal graph boxes represents time and is most conveniently represented as a number of update periods with the current update period at the far right-hand edge of the graph. Earlier update periods occur further to the left. A constant number of update periods is shown in each graph box to the left of the current update period. As a result, the time axis appears to shift leftward to always keep the current update period at the far right-hand side of each parameter graph box for its total power ratio graph for the corresponding electroencephalographic signal.

The number in the upper left-hand corner of each graph box for each electroencephalographic signal is the power drop index or PDI which serves to represent the extent and duration of power reductions measured in its corresponding electroencephalographic signal. This parameter too is an indicator of any significant insufficiencies occurring in the cerebral perfusion of the patient. The PDI is provided as a succession of values, one in each index period in which it is calculated. Such an index period need not be the same as an update period but can conveniently be chosen to be the same, this being the basis for the display graphs shown in FIGS. 3A-3C.

The power drop index, or PDI, corresponding to a single electroencephalographic signal for the $p^{th}$ index period is found from the following:

$$PDI_{p(m)} = PDI_{p(m-1)} + cg_{int}\left[\frac{T - 100\frac{P_m}{P_{base}}}{R}\right]$$

Here again p is a counting index which counts the number of periods of duration v at the end of each of which the index is updated by recalculating its values based on the then current value of $P_m$. As indicated above, m is also a counting index for counting the number of update periods of duration u, but since update period u need not be equal in time to the index recalculation period v, m need not equal p. However, p will be related to m and so is shown in the last equation above as a function of m. The function $g_{int}$ provides an integer value which depends on its argument.

As can be seen from the equation for PDI, the value of PDI in the current $p^{th}$ period is equal to its value in the preceding period plus the change from the preceding period to the present period as calculated through the right-hand term on the right side of this equation. This change term can be seen to depend on the ratio of total power $P_m$ to the reference or base power $P_{base}$ for the $m^{th}$ update period which period coincides with some part of the current index period. Just in which part of an index period P a value for $P_m$ is taken in corresponding to an update period depends on the arrangement used in signal processing means 16. Differing arrangements for determining the value of PDI in the $p^{th}$ period can yield differing results if the index period v is not equal to the update period u. Thus, there can be a slight difference in the value obtained for the PDI from one implementation to another depending on how the corresponding signal processing modules in the two implementations are directed to calculate such values.

A further complication can arise where the update period and the index period are not the same due to the nature of the expression above for the PDI. Because that expression is cumulative in the sense that it can provide a change to the existing value of the index found in the preceding period, the number of times the value for the PDI is recalculated affects the value currently found. That is, if the right-hand term on the right side of the expression for the PDI has a value, that value will be added into the PDI as often as the recalculation of the PDI occurs. Hence, the value found for the PDI will vary depending on the magnitude of v versus u. If having u equal v, and so leaving m and p equal, is chosen as a reference, then the situation where v is greater than u leads to a value for the PDI which is less than it would be in the reference situation. The reverse situation of u greater than v would lead to a greater value for the PDI than in the reference situation.

The PDI, in the situation where v does not equal u, can be adjusted to have or nearly have the value it would have had in the reference situation where v does equal u. A correction factor, c, has been introduced in the right-hand term of the right-hand side of the equation for the PDI above for this purpose. A mathematical expression for correction factor c could take a wide variety of forms depending on what differences in values are estimated occur between the PDI found for the situation with difference between periods u and v and the reference situation with u equal to v. If the circumstances for monitoring electroencephalographic signals of a patient undergoing surgery are such that the right-hand factor on the right-hand side of the equation above for the PDI is not expected to change much over the index period v, then correction factor c can be taken to be p/m or v/u to give a reasonably accurate correction of the PDI to the value it would have had in the reference situation. In other situations, a statistical estimator can be developed appropriate to that situation and used.

The PDI always has an integer value because, as indicated above, of the nature of the function $g_{int}$ in the PDI expression. This function transforms positive numbers greater than zero in its argument to the next smallest integer that is greater than that argument value, unless the argument is already an integer in which situation the value is left as it is. Should the argument of $g_{int}$ be zero or a negative number, that argument is then transformed to a value of zero.

The argument of $g_{int}$ has a threshold, T, written in percent from which is subtracted the ratio of the total power $P_m$ for the $m_{th}$ period divided by the reference or base total power $P_{base}$ also written as a percent. Thus, this argument will always be negative unless the ratio $P_m/P_{base}$ times 100 becomes less than the threshold value T. As a result, there will never be any additions to the PDI value of a previous period until the total power in the $m_{th}$ update period for the corresponding electroencephalographic signal has dropped sufficiently below the base line reference power for the ratio of these two to be below the value set for threshold T. The value of the threshold will be set by an operator of the system based on his experience in the circumstances in which the patient is being operated on, taking into account such factors as the level of hypothermia or the nature of the anesthetic or surgical technique, or both.

The numerator, $T - P_m/P_{base}$, in the argument of $g_{int}$ is divided by the resolution, R. Since R sets the value at which the numerator will cause the argument to be unity, and every integral multiple thereof, the value of R in effect sets the number of integers which will occur between the value of the threshold T and zero, thereby dividing this range into as many parts as desired. The greater the number of integers, the faster the PDI will grow for the values of the ratio $P_m/P_{base}$. Because $g_{int}$ provides only positive integers, the PDI can only increase, that is, can only change monotonically. The rate of that growth for various ratios of $P_m/P_{base}$ will be set by the value chosen for R. If T is chosen to be 40%, as it is in FIGS. 3A-3C, and R is chosen to have a value of five, the following table would result for $g_{int}$:

| Range of $P_m/P_{base}$ | $g_{int}$ |
|---|---|
| .40–.35 | 1 |
| .35–.30 | 2 |
| .30–.25 | 3 |
| .25–.20 | 4 |
| .20–.15 | 5 |
| .15–.10 | 6 |
| .10–.05 | 7 |
| .05–.00 | 8 |

Figure 3A:
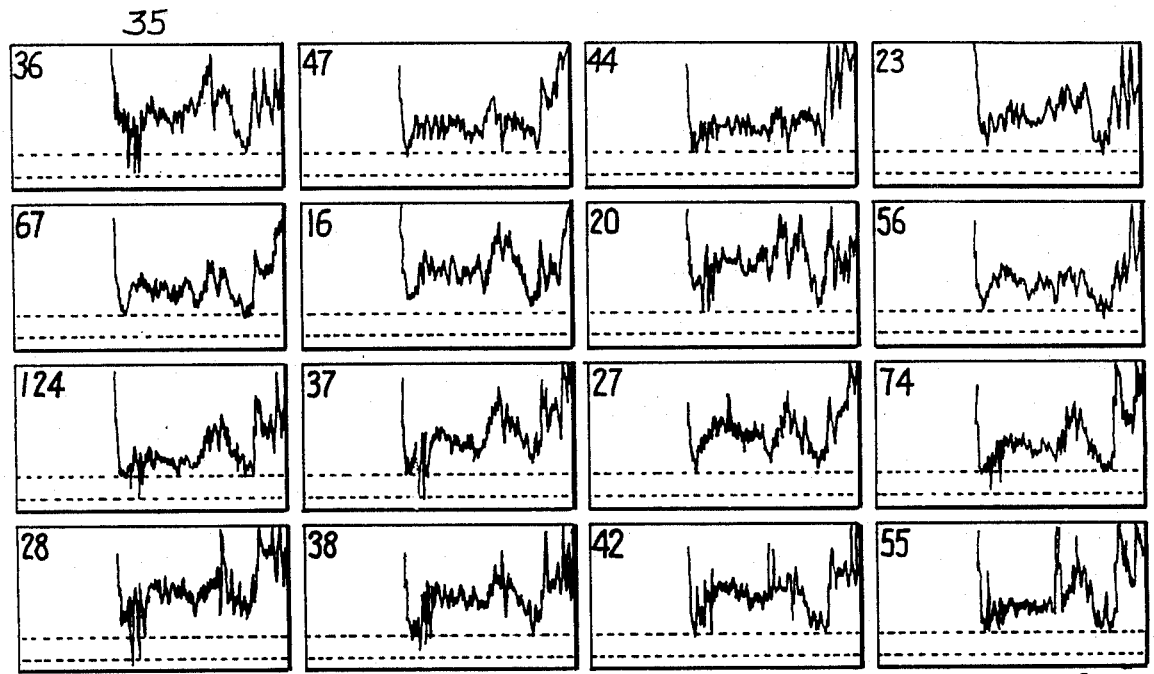
FIGS. 3A-C show displays provided by the system of FIG. 1.
Figure 3B:
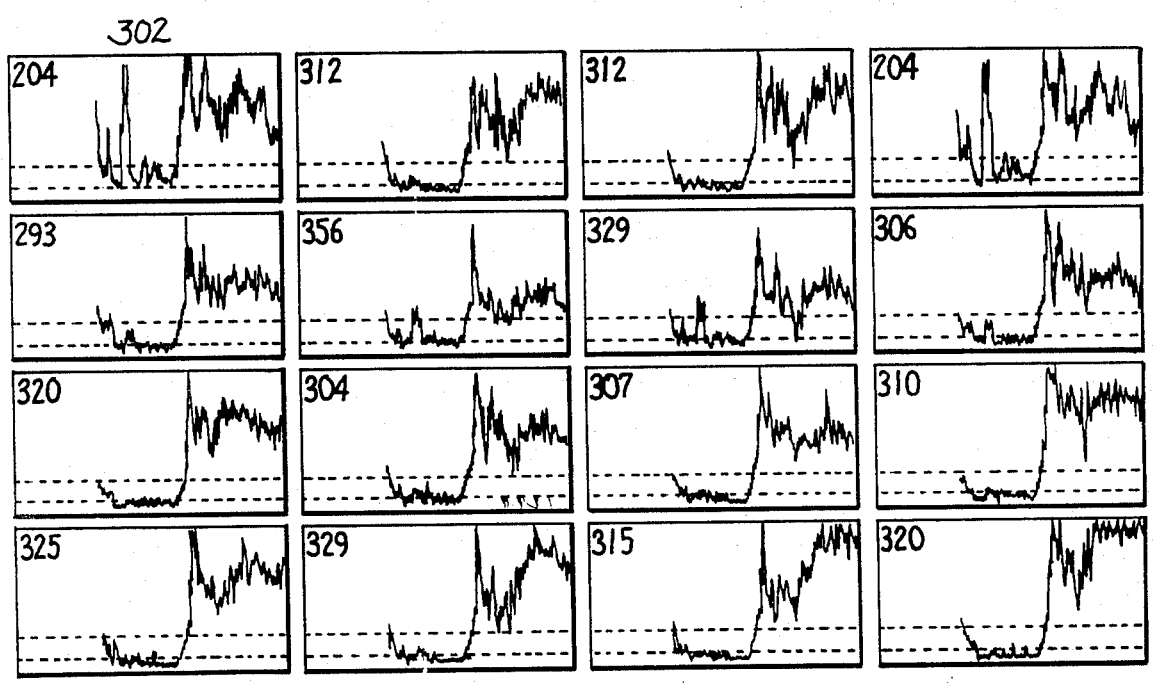
Figure 3C:
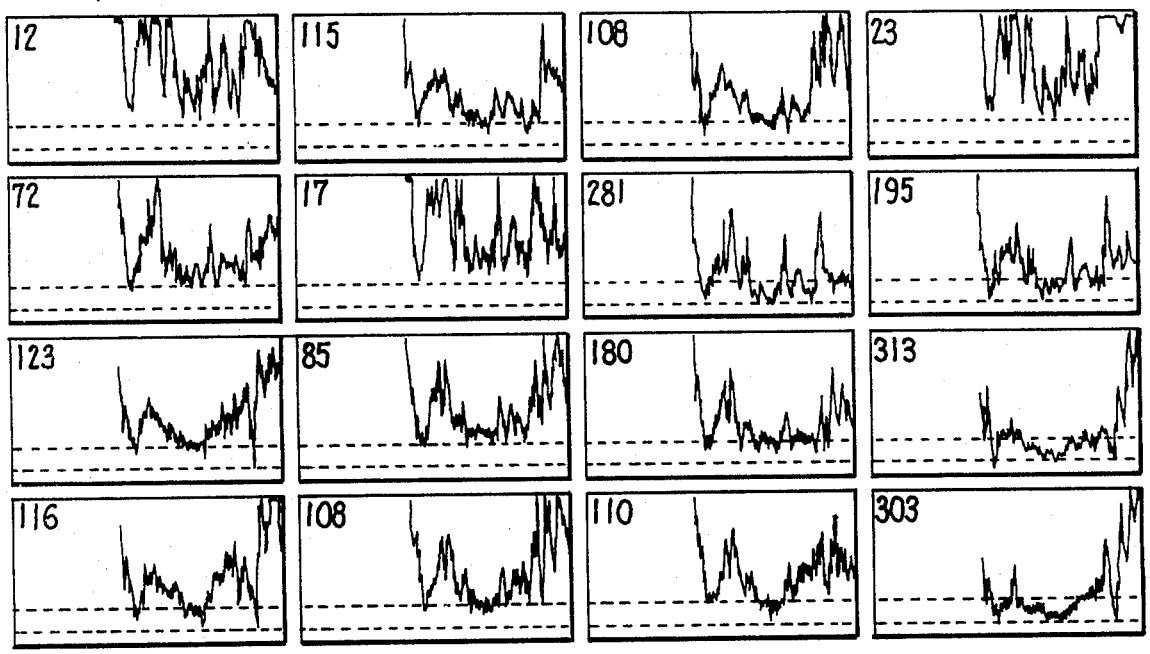

Though the numerator terms are written in percent to facilitate comparison thereof with the graphs shown FIGS. 3A-3C, the numerator can clearly be left in fractional form with the fractional value choice for the threshold T. The resolution R would be chosen accordingly to give the desired number of subdivisions of the value range between T and zero.

FIGS. 3A-3C show graphs of total powers and the power drop indices for 16 electroencephalographic signals taken at the heads of three different patients having undergone open-heart surgery, the results for one patient being shown in each figure. The threshold values are set at 40% for the power drop indices and the resolution values are set at five. Also, the index period and the update periods are chosen to be equal to one another and of a duration of one minute. The sampling rate was chosen to be 256 samples per second. The graphs toward the top in each figure for each corresponding patient are obtained from electroencephalographic signals obtained from more frontal portions of that patient's head while those at the bottom of the figure are from signals obtained at the rear of that patient's head. Similarly, the left-hand graphs in the figures represent the left side of the corresponding patient's head, while the right-hand graphs represent signals from the right side of that patient's head.

FIG. 3A is of a male who shows a relatively small power drop index value in each of the graph boxes in that figure representing an individual electroencephalographic signal, and so the electroencephalographic signal power drops are small over the entire patient's head for the time duration involved. This male had no postoperative neurologic deficit. The graphs in this figure cover a time duration of one hour and 49 minutes. The number in the upper left-hand corner of the entire display above all of the boxes represents the results of averaging over all 16 of the electroencephalographic signals being obtained and over all obtained in the base line or reference data gathering process. Composite successions of total powers can be found from these signals to provide a composite reference power and a composite signal power drop index as shown in the upper left-hand corners of the displays.

In FIG. 3B, the second patient, a male, has some very large values for the various power indices, and large values are true in every graph box in the display indicating that there were substantial electroencephalographic signal power drops measured over the entire area of the patient's head. This clearly calls for the operator, or operating room associates, to increase the pump flow at some point in the duration shown to increase the mean arterial blood pressure of this patient to improve cerebral perfusion. Such an action would very likely prevent the PDI from reaching such values and thus avoid brain damage. This male was found after the operation to suffer from diffuse cerebral dysfunction. The graphs in this figure cover one hour and 58 minutes.

FIG. 3C shows a female who has suffered a postoperative right parietal lobe stroke. Much larger values are found for the power drop indices on the right-hand side as compared to those on the left-hand side. Such a situation also suggests that increasing the mean arterial pressure may be in order, or readjusting the arterial cannula to assure adequate cerebral perfusion.

Although the present invention has been described with reference to preferred embodiments, workers skilled in the art will recognize that changes may be made in form and detail without departing from the spirit and scope of the invention.

What is claimed is:

1. A method of treating at least a first electroencephalographic signal to provide a first index parameter based thereon indicative of extent and durations of selected diminutions in power in such signal, said method comprising:

acquiring said first electroencephalographic signal;

determining a first succession of total powers of said first electroencephalographic signal with there being one of said total powers associated with each of an ordered set of selected segments of said first electroencephalographic signal which are in order of occurrence thereof; and forming said first index parameter as a succession of values depending on said first succession of total powers with said successive first index parameter values changing monotonically, if at all.

2. The method of claim 1 wherein said acquiring of said first electroencephalographic signal further comprises acquiring a first sequence of consecutive samples of amplitude values of said first electroencephalographic signal taken at a rate sufficient for them to represent that signal, said first sequence also comprising a plurality of successive, selected first sequence subsequences each corresponding to a said segment, and wherein said determining of a first succession of total powers further comprises forming a first succession of frequency domain power spectra with there being one of said frequency domain power spectra in said first succession thereof formed for each of selected ones of said first sequence subsequences; and wherein said determining of a first succession of total powers further comprises:

forming a first succession of average frequency domain power spectra with each said average frequency domain power spectrum in said first succession thereof comprising a plurality of frequency components each being formed by an amplitude average of frequency components of a common frequency obtained from selected ones of said first succession of frequency domain power spectra; and determining a first succession of total powers with there being one of said total powers determined for each of selected ones of said average frequency domain power spectra in said first succession thereof.

3. The method of claim 2 wherein said acquiring of said first sequence of consecutive samples of amplitude values of said first electroencephalographic signal occurs in a first time duration, and wherein said method further comprises:

acquiring a second sequence of consecutive samples of amplitude values of said first electroencephalographic signal during a second time duration taken at a rate sufficient for them to represent that signal, said second sequence also comprising a plurality of successive selected second sequence subsequences;

forming a second succession of frequency domain power spectra with there being one of said frequency domain power spectra in said second succession thereof formed for each of selected ones of said second sequence subsequences;

forming a second succession of average frequency domain power spectra with each said average frequency domain power spectrum in said second succession thereof comprising a plurality of frequency components each being formed by an amplitude average of frequency components of a common frequency obtained from selected ones of said second succession of frequency domain power spectra;

determining a second succession of total powers with there being one of said total powers determined for each of selected ones of said average frequency domain power spectra in said second succession thereof.

4. The method of claim 3 wherein selected ones of said second succession of total powers are used in forming an average total power to provide a total power reference value.

5. The method of claim 4 wherein said successive index parameter values depend on said first succession of total powers each divided by said total power reference value.

6. The method of claim 5 wherein said index parameter values change only if at least some ratios, formed by said total powers in said first succession thereof divided by said total power reference value, have values below a selected threshold value.

7. The method of claim 6 wherein a successive index parameter value is formed for each total power in said first succession thereof.

8. The method of claim 6 wherein ratios are formed by said total powers in said first succession thereof being divided by said total power reference value and wherein said successive index parameter values change by greater amounts for those said ratios on which they depend having values relatively farther below said threshold value than do successive index parameter values which depend on those of said ratios having values relatively closer to said threshold value.

9. The method of claim 8 wherein any change in value between a pair of successive values of a said index parameter is made by an increment to that one preceding in said pair.

10. The method of claim 9 wherein a successive index parameter value is formed for each total power in said first succession thereof.

11. The method of claim 5 wherein said first electroencephalographic signal is obtained from a subject's head to whose brain there is a flow of blood under external control to at least some extent, and said forming of said first index parameter is followed by adjusting said flow of blood based on values of said first index parameter.

12. The method of claim 4 wherein said forming said first index parameter as a succession of values is followed after each value is formed in said succession thereof by displaying a then current value of said first index parameter, and by displaying a representation of said first succession of total powers each divided by said total power reference value.

13. The method of claim 2 wherein there is a plurality of electroencephalographic signals including said first electroencephalographic signal and wherein said method further comprises:

acquiring a first plurality of sequences, including said first sequence, of consecutive samples of amplitude values of corresponding ones of said plurality of electroencephalographic signals with each said sequence in said first plurality thereof taken at a rate sufficient for it to represent that electroencephalographic signal corresponding thereto, said first plurality of sequences also each comprising a plurality of successive, selected subsequences including said first sequence subsequences;

forming a first plurality of successions of frequency domain power spectra including said first succession of said frequency domain power spectra, there being a said succession of frequency domain power spectra corresponding to each said sequence in said first plurality thereof with there being one of said frequency domain power spectra in each succession thereof formed for each of selected ones of said subsequences in that said sequence corresponding thereto;

forming a first plurality of successions of average frequency domain power spectra including said first succession of average domain power spectra, there being a said succession of average frequency domain power spectra corresponding to each said succession of frequency domain power spectra in said first plurality thereof with each said average frequency domain power spectrum in each said succession thereof comprising a plurality of frequency components each being formed by an amplitude average of frequency components of a common frequency obtained from selected ones of said frequency domain power spectra in that said succession of frequency domain power spectra corresponding thereto;

determining a first plurality of successions of total powers including said first succession of total powers, there being a said succession of total powers corresponding to each said succession of average frequency domain power spectra in said first plurality thereof with there being one of said total power in a said succession thereof determined for each of selected ones of said average frequency domain power spectra in that said succession of average frequency domain spectra corresponding thereto; and providing a plurality of index parameters including said first index parameter, there being a said index parameter corresponding to each said succession of said total powers in said plurality thereof with each said index parameter formed as a succession of values depending on that said succession of total powers corresponding thereto, with said successive index parameter values for each said index parameter changing monotonically, if at all.

14. The method of claim 13 wherein said acquiring of said first plurality of sequences of consecutive samples of amplitude values of corresponding ones of said plurality of electroencephalographic signals occurs in a first time duration, and wherein said method further comprises:

acquiring a second plurality of sequences of consecutive samples of amplitude values of corresponding ones of said plurality of electroencephalographic signals during a second time duration with each said sequence in said second plurality thereof taken at a rate sufficient for it to represent that electroencephalographic signal corresponding thereto, said second plurality of sequences also each comprising a plurality of consecutive selected subsequences;

forming a second plurality of successions of frequency domain power spectra, there being a said succession of frequency domain power spectra corresponding to each said sequence in said second plurality thereof with there being one of said frequency domain power spectra in each said succession thereof formed for each of selected ones of said subsequences in that said sequence corresponding thereto;

forming a second plurality of successions of average frequency domain power spectra, there being a said succession of average frequency domain power spectra corresponding to each said succession of frequency domain power spectra in said second plurality thereof with each said average frequency domain power spectrum in each said succession thereof comprising a plurality of frequency components each being formed by an amplitude average of frequency components of a common frequency obtained from selected ones of said frequency domain power spectra in that said corresponding succession of frequency domain power spectra corresponding thereto; and determining a second plurality of successions of total powers, there being a said succession of total powers corresponding to each said succession of average frequency domain power spectra in said second plurality thereof with there being one of said total power in a said succession thereof determined for each of selected ones of said average frequency domain power spectra in that said succession of average frequency domain power spectra corresponding thereto.

15. The method of claim 14 wherein selected ones of each of said successions of total powers in said second plurality thereof are used in forming a corresponding average total power to provide a total power reference value corresponding to that said succession of total powers.

16. The method of claim 15 wherein said successive index parameter values of each said plurality of index parameters depend on that corresponding one of said successions of total powers in said first plurality thereof with each total power therein divided by that said total power reference value corresponding thereto.

17. The method of claim 16 wherein said index parameter values of each of said plurality of index parameters change only if at least some corresponding ratios, formed by said total powers in that corresponding succession thereof divided by said total power reference value corresponding to that succession, have values below selected corresponding threshold values.

18. The method of claim 17 wherein a successive index parameter value for each index parameter in said plurality thereof is provided for each total power in that corresponding said succession thereof.

19. The method of claim 17 wherein ratios are formed by said total powers in each of said successions of total powers being divided by said total power reference value corresponding to that succession and wherein said successive index parameter values of each of said plurality of index parameters change by greater amounts for those corresponding ratios on which they depend having values relatively farther below said corresponding threshold values than do successive index parameter values of each of said plurality of index parameters which depend on those corresponding ratios having values related closer to said corresponding threshold values.

20. The method of claim 19 wherein any change in value between a successive pair of values of a said index parameter is made by an increment to that one preceding in said pair.

21. The method of claim 20 wherein a successive index parameter value for each index parameter in said plurality thereof is provided for each total power in that corresponding said succession thereof.

22. The method of claim 16 wherein said plurality of electroencephalographic signals are obtained from a subject's head to whose brain there is a flow of blood under external control to at least some extent, and said forming of said plurality of index parameters is followed by adjusting said flow of blood based on values of said plurality of index parameters.

23. The method of claim 15 wherein said providing a plurality of index parameters with each said index parameter being formed as a succession of values is followed after each value is formed in said succession thereof for such an index parameter by displaying a then current value of that index parameter, and by displaying a representation of its corresponding succession of total powers where each total power therein is divided by that said total power reference value corresponding thereto.

24. The method of claim 2 wherein said index parameter values change only if at least some of said total powers in said first succession thereof have values less than a selected threshold value.

25. The method of claim 24 wherein a successive index parameter value is formed for each total power in said first succession thereof.

26. The method of claim 24 wherein said successive index parameter values change by greater amounts for those said total powers on which they depend having values relatively farther below said threshold value than do successive index parameter values which depend on those of said total powers relatively closer to said threshold value.

27. The method of claim 26 wherein any change in value between a successive pair of values of a said index parameter is made by an increment to that one preceding in said pair.

28. The method of claim 27 wherein a successive index parameter value is fiormed for each total power in said first succession thereof.

29. The method of claim 2 wherein said forming said first index parameter as a succession of values is followed after each value is formed in said succession thereof by displaying a then current value of said first index parameter, and by displaying a representation of said first succession of total powers.

30. The method of claim 2 wherein said first electroencephalographic signal is obtained from a subject's head to whose brain there is a flow of blood under external control to at least some extent, and said forming of said first index parameter is followed by adjusting said flow of blood based on values of said first index parameter.

31. A method of treating electroencephalographic signals to provide index parameters based thereon indicative of extents and durations of selected diminutions in power in such signals, said method comprising acquiring a plurality of electroencephalographic signals determining a plurality of total powers there being a said succession of total powers corresponding to each of said electroencephalographic signals in said plurality thereof with there being one of said total powers in each succession thereof associated with each of an ordered set of selected segments of that electroencephalographic signal corresponding thereto which are in order of occurrence thereof; and providing a plurality of index parameters, there being a said index parameter corresponding to each said succession of said total powers in said plurality thereof with each said index parameter formed as a succession of values depending on that said succession of total powers corresponding thereto, with said successive index parameter values for each said index parameter changing monotonically, if at all.

32. The method of claim 1 and further comprising:

determining a first signal plurality of successions of segment total powers of said first electroencephalographic signal with there being one of said successions of segment total powers in said first signal plurality thereof associated with each said segment; and forming each of said first succession of total powers by averaging a corresponding said succession of segment total powers.

33. The method of claim 32 wherein there is a plurality of electroencephalographic signals including said first electroencephalographic signal and wherein said method further comprises:

acquiring a first plurality of sequences of consecutive samples of amplitude values of corresponding ones of said plurality of electroencephalographic signals with each said sequence in said first plurality thereof taken at a rate sufficient to represent that electroencephalographic signal corresponding thereto, said first plurality of sequences also each comprising a plurality of successive, selected subsequences each corresponding to a said segment;

forming a first plurality of successions of frequency domain power spectra, there being a said succession of frequency domain power spectra corresponding to each said sequence in said first plurality thereof with there being one of said frequency domain power spectra in each succession thereof formed for each of selected ones of said subsequences in that said sequence corresponding thereto;

determining multiple signal pluralities of successions of segment total powers, including said first plurality of successions of total powers, there being a said signal plurality of successions of segment total powers corresponding to each said succession of frequency domain power spectra in said first plurality thereof with each said segment total power in each said signal plurality of successions thereof comprising an amplitude average of frequency components of a corresponding one of said frequency domain power spectra in that said succession of frequency domain spectra corresponding thereto;

forming a plurality successions of total powers, there being a said succession of total powers to each said signal plurality of successions of segment total powers in said multiplicity thereof with each total power in said plurality thereof formed by averaging segment total powers in each succession thereof in that said signal plurality of successions of segment total powers corresponding thereto; and providing a plurality index parameters, there being a said index parameter corresponding to each said succession of said total powers in said plurality thereof with each said index parameter formed as a succession of values depending on said succession of total powers corresponding thereto, with said successive index parameter values for each said index parameter changing monotonically, if at all.

34. The method of claim 1 wherein said index parameter values change only if at least some of said total powers in said first succession thereof have values less than a selected threshold value.

35. The method of claim 34 wherein a successive index parameter value is formed for each total power in said first succession thereof.

36. The method of claim 34 wherein said successive index parameter values change by greater amounts for those said total powers on which they depend having values relatively farther below said threshold value than do successive index parameter values which depend on those of said total powers having values relatively closer to said threshold value.

37. The method of claim 36 wherein any change in value between a successive pair of values of a said index parameter is made by an increment to that one preceding in said pair.

38. The method of claim 37 wherein a successive index parameter value is formed for each total power in said first succession thereof.

39. The method of claim 1 wherein said forming said first index parameter as a succession of values is followed after each value is formed in said succession thereof by displaying a then current value of said first index parameter, and by displaying a representation of said first succession of total powers.

40. The method of claim 1 wherein said first electroencephalographic signal is obtained from a subject's head to whose brain there is a flow of blood under external control to at least some extent, and said forming of said first index parameter is followed by adjusting said flow of blood based on values of said first index parameter.

41. A monitoring system for providing an index parameter depending on at least a first electroencephalographic signal which is indicative of extent and duration of selected diminutions in power in such signal, said system comprising:

a signal acquiring means for acquiring said first electroencephalographic signal;

an analog-to-digital converter means electrically connected to said signal acquiring means for providing a first sequence of consecutive digitized samples of amplitude values of said first electroencephalographic signal;

a signal processing means electrically connected to said analog-to-digital converter means capable of forming a first succession of frequency domain power spectra for selected successive subsequences of said first sequence as a basis for forming a first succession of average frequency domain power spectra provided by forming an average of common frequency components of selected ones of said frequency domain power spectra in said first succession thereof, a total power being found for each selected one of said average frequency domain power spectra to form a first succession of total powers, said signal processing means forming a first index parameter as a succession of values depending on said first succession of total powers with said successive first index parameter values changing monotonically, if at all; and a display means electrically connected to said signal processing means for indicating said first index parameter values.

42. The apparatus of claim 41 wherein said signal acquiring means is capable of acquiring a plurality of electroencephalographic signals including said first electroencephalographic signal for each of which said analog-to-digital converter means provides a corresponding sequence of consecutive digitized samples of its amplitude values which are submitted to said signal processing means to form corresponding index parameters, including said first index parameter, in that same manner as said first index parameter is formed.

43. The apparatus of claim 41 wherein said display means is capable of providing a visual display representing said first succession of total powers and a current value of said first index parameter.

* * * * *

UNITED STATES PATENT AND TRADEMARK OFFICE
CERTIFICATE OF CORRECTION

PATENT NO. : 4,817,627

DATED : April 4, 1989

INVENTOR(S) : Daniel E. Cohen et al.

It is certified that error appears in the above-identified patent and that said Letters Patent is hereby corrected as shown below:

Column 11, line 34, delete "durations" and therefore insert --duration--.

Column 12, line 2, delete "selected" and therefore insert --selecting--.

Column 12, line 39, delete "selected" and therefore insert --selecting--.

Column 16, line 4, delete "fiormed" and therefore insert --formed--.

Column 16, line 22, following "comprising" insert --;--.

Column 16, lines 23-24, following "signals" insert --;--.

Signed and Sealed this

Twentieth Day of February, 1990

*Attest:*

JEFFREY M. SAMUELS

*Attesting Officer*   Acting Commissioner of Patents and Trademarks